United States Patent
Faltys et al.

(10) Patent No.: US 7,444,185 B1
(45) Date of Patent: Oct. 28, 2008

(54) HIGH CONTACT COUNT, SUB-MINIATURE, FULLY IMPLANTABLE COCHLEAR PROSTHESIS

(75) Inventors: Michael A Faltys, Northridge, CA (US); Glen A Griffith, Newbury Park, CA (US); William VanBrooks Harrison, Valencia, CA (US)

(73) Assignee: Advanced Bionics, LLC, Valencia, CA (US)

( * ) Notice: Subject to any disclaimer, the term of this patent is extended or adjusted under 35 U.S.C. 154(b) by 44 days.

(21) Appl. No.: 11/234,506

(22) Filed: Sep. 23, 2005

Related U.S. Application Data (60) Continuation of application No. 10/624,724, filed on Jul. 21, 2003, now Pat. No. 6,980,864, which is a division of application No. 09/823,271, filed on Mar. 30, 2001, now Pat. No. 6,826,430.

(60) Provisional application No. 60/203,707, filed on May 11, 2000, provisional application No. 60/193,647, filed on Mar. 31, 2000.

(51) Int. Cl.
*A61N 1/18* (2006.01)
*A61N 1/05* (2006.01)

(52) U.S. Cl. ............................ 607/137; 607/57; 607/56

(58) Field of Classification Search ............. 607/55–57, 607/137; 623/10
See application file for complete search history.

(56) References Cited

U.S. PATENT DOCUMENTS

| | | | |
|---|---|---|---|
| 3,764,748 A * | 10/1973 | Branch et al. | 607/57 |
| 4,532,930 A * | 8/1985 | Crosby et al. | 607/57 |
| 4,592,359 A | 6/1986 | Galbraith | |
| 4,628,934 A | 12/1986 | Pohndorf et al. | |
| 4,729,366 A | 3/1988 | Schaefer | |
| 4,947,844 A | 8/1990 | McDermott | |
| 5,000,194 A | 3/1991 | van den Honert et al. | |
| 5,105,811 A | 4/1992 | Kuzma | |
| 5,443,493 A | 8/1995 | Byers et al. | |
| 5,470,348 A | 11/1995 | Neubauer et al. | |
| 5,549,658 A * | 8/1996 | Shannon et al. | 607/57 |
| 5,571,148 A | 11/1996 | Loeb et al. | |
| 5,603,726 A | 2/1997 | Schulman et al. | |
| 5,649,970 A | 7/1997 | Loeb et al. | |
| 5,775,172 A | 7/1998 | Fevre et al. | |
| 5,814,095 A | 9/1998 | Muller et al. | |
| 5,833,714 A | 11/1998 | Loeb | |
| 5,957,958 A * | 9/1999 | Schulman et al. | 607/56 |
| 6,002,966 A | 12/1999 | Loeb et al. | |

(Continued)

FOREIGN PATENT DOCUMENTS

DE 19829637 A1 7/1998

(Continued)

*Primary Examiner*—Kennedy J. Schaetzle
*Assistant Examiner*—Natasha N Patel
(74) *Attorney, Agent, or Firm*—Bryant R. Gold (57) ABSTRACT

An active electrode array provides a programmable number of electrode contacts through which stimulation current may be selectively delivered to surrounding tissue, preferably through the use of appropriate stimulation groups. The active electrode array provides a large number of both medial and lateral contacts, any one of which may be selected to apply a stimulus pulse through active switching elements included within the array. The active switching elements included within the array operate at a very low compliance voltage, thereby reducing power consumption.

5 Claims, 6 Drawing Sheets

U.S. PATENT DOCUMENTS

| | | | |
|---|---|---|---|
| 6,002,969 A | 12/1999 | Machek et al. | |
| 6,011,993 A | 1/2000 | Tziviskos et al. | |
| 6,067,474 A | 5/2000 | Schulman et al. | |
| 6,217,508 B1 | 4/2001 | Ball et al. | |
| 6,236,889 B1 | 5/2001 | Soykan et al. | |
| 6,289,247 B1 * | 9/2001 | Faltys et al. | 607/57 |
| 6,355,064 B1 | 3/2002 | Peeters et al. | |
| 6,473,653 B1 | 10/2002 | Schallhorn et al. | |
| 6,980,864 B2 * | 12/2005 | Faltys et al. | 607/116 |

FOREIGN PATENT DOCUMENTS

| | | |
|---|---|---|
| DE | 19915846 C1 | 4/1999 |
| WO | WO 97/01314 A1 | 1/1997 |
| WO | WO 01/74278 A3 | 10/2001 |

* cited by examiner

HIGH CONTACT COUNT, SUB-MINIATURE, FULLY IMPLANTABLE COCHLEAR PROSTHESIS

The present application is a Continuation of application Ser. No. 10/624,724, filed Jul. 21, 2003; which is a Divisional of U.S. application Ser. No. 09/823,271, filed Mar. 30, 2001, now issued as U.S. Pat. No. 6,826,430; which claims the benefit of U.S. Provisional Application Ser. No. 60/193,647, filed Mar. 31, 2000; and U.S. Provisional Application Ser. No. 60/203,707, filed May 11, 2000, which applications are incorporated herein by reference.

BACKGROUND OF THE INVENTION

The present invention relates to implantable devices, and more particularly, to a fully implantable device or system for stimulating or sensing living tissue. The implantable device includes a rechargeable battery or other replenishable power source. More particularly, the present invention relates to a fully implantable cochlear implant system (FICIS) that allows profoundly deaf persons to hear sounds without the need for wearing or carrying external (non-implanted) hearing devices or components.

Presently available implantable stimulation devices, such as a cochlear implant device or a neural stimulator, typically have an implanted unit, an external ac coil, and an external control unit and power source. The external control unit and power source includes a suitable control processor and other circuitry that generates and sends the appropriate command and power signals to the implanted unit to enable it to carry out its intended function. The external control unit and power source are powered by a battery that supplies electrical power through the ac coil to the implanted unit via inductive coupling for providing power for any necessary signal processing and control circuitry and for electrically stimulating select nerves or muscles. Efficient power transmission through a patient's skin from the external unit to the implanted unit via inductive coupling requires constant close alignment between the two units.

Representative prior art cochlear implant systems are disclosed, e.g., in U.S. Pat. Nos. 4,532,930; 4,592,359; 4,947,844; 5,776,172; and 6,067,474, all of which are incorporated herein by reference.

Disadvantageously, each of the known prior art cochlear stimulation systems, with the exception of some embodiments of the system disclosed in the U.S. Pat. No. 6,067,474 patent, requires the use of an external power source and speech processing system, coupled to the implanted stimulation device. For many patients, achieving and maintaining the required coupling between the external components and the implanted component can be troublesome, inconvenient, and unsightly. Thus, there exists a need and desire for a small, lightweight fully implantable device or system that does not require an external unit in order to be fully functional, that does not need constant external power, and that includes a long-lasting internal battery that may be recharged, when necessary, within a relatively short time period.

Moreover, even if a rechargeable battery were available for use within an implantable cochlear stimulation system, such rechargeable battery must not significantly alter the size of the existing implantable cochlear stimulator. This is because the curvature and thickness of the skull is such that there is only a limited amount of space wherein a surgeon may form a pocket wherein a cochlear stimulator may be implanted. This is particularly an acute problem for young children, where the thickness of the skull is relatively thin and the curvature of the skull is greater than for an adult. Thus, there is a need for a fully implantable cochlear implant system that is adaptable and lends itself for implantation within a range of head sizes and shapes.

Additionally, even where a rechargeable battery is employed within a fully implantable cochlear implant system, which fully implantable system includes an implantable speech processor and microphone, it may be necessary or desirable, from time to time, to replace the battery and/or to upgrade the speech processor hardware. Because implantation of the cochlear implant system, including insertion of the delicate electrode array into the cochlea of the patient, represents major surgery, which major surgery would hopefully only need to be performed once in a patient's lifetime, it is seen that there is also a need for a fully implantable cochlear implant system wherein at least the battery, and perhaps even some or all of the speech processing circuitry, may be replaced or upgraded from time to time through minimal invasive surgery, while leaving the delicate cochlear electrode array intact for use with the replaced battery and/or upgraded speech processor.

BRIEF SUMMARY OF THE INVENTION

The present invention addresses the above and other needs by providing a fully implantable cochlear prosthesis that includes (1) an implantable hermetically sealed case wherein electronic circuitry, including an implantable microphone, are housed, (2) an active electrode array that provides a programmable number of electrode contacts through which stimulation current may be selectively delivered to surrounding tissue, and (3) a connector that allows the active electrode array to be detachably connected with the electronic circuitry within the sealed case.

In accordance with one aspect of the invention, the active electrode array provides a plurality of groups of electrodes, each electrode having both medial and lateral contacts, any one of which may be selected to apply a stimulus pulse through active switching elements included within the array, preferably through the use of Stimulation Groups.

In accordance with another aspect of the invention, the active switching elements included within the array operate at a very low compliance voltage, thereby reducing power consumption.

In accordance with still another aspect of the invention, radial stimulation may be provided by the active electrode array in order to increase selectivity.

In accordance with yet another aspect of the invention, the entire prosthesis is very efficient from a power consumption standpoint, thereby allowing a smaller battery to power the system for longer periods of time before recharging or replacement is required.

In accordance with a further aspect of the invention, the hermetically sealed case within which the electronic circuitry, battery, and microphone are housed may be replaced, when needed, through minimally invasive surgery.

In accordance with an additional aspect of the invention, the electronic circuitry housed within the hermetically sealed case may be programmed or adjusted, e.g., upgraded, as needed, using either RF or acoustic control signals received through an implantable coil or an implantable microphone. In a preferred embodiment, acoustic control signals are realized using phase-shift keyed (PSK) modulation of an acoustic signal within a very narrow band centered at about 6 KHz.

It is thus an object of the present invention to provide a fully implantable tissue stimulation prosthesis that utilizes an active electrode array.

It is another object of the invention to provide such a fully implantable prosthesis that includes both digital and analog circuits, any one or all of which may be used depending upon the selected mode of operation.

BRIEF DESCRIPTION OF THE DRAWINGS

The above and other aspects, features and advantages of the present invention will be more apparent from the following more particular description thereof, presented in conjunction with the following drawings wherein:

FIG. 1 is a functional block diagram of a fully implantable cochlear prosthesis made in accordance with the present invention (which figure is split into two halves, one being denoted FIGS. 1-1 and the other FIGS. 1-2);

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

While the invention described herein is presented in terms of a cochlear prosthesis, it is to be understood that a cochlear prosthesis is only one example of numerous different types of prosthesis and applications that may benefit from the invention. That is, the cochlear prosthesis described herein is, in reality, a neural stimulator, and such neural stimulator may also be used for applications other than stimulation of the cochlea. For example, the prosthesis described herein may be used to selectively stimulate any tissue or nerves throughout a patient's body for a wide variety of applications, including deep brain stimulation, stimulation to control urinary incontinence, stimulation to manage pain, stimulation to control various nervous disorders and diseases, and the like. Further, it is to be understood that the active electrode described herein, while intended for insertion into a human cochlea, may also be used for many other types of applications. All such other types of applications are considered to fall within the scope of the present invention.

The following patents disclose information relevant to the design, use and operation of a fully implantable cochlear stimulation system: U.S. Pat. No. 5,603,726; U.S. Pat. No. 6,002,966; U.S. patent application Ser. No. 09/407,826, filed Sep. 28, 1999, now issued as U.S. Pat. No. 6,272,382; U.S. patent application Ser. No. 09/322,712, filed May 28, 1999, now issued as U.S. Pat. No. 6,289,247; which patents are incorporated herein by reference.

In order to provide a miniature, low power, cochlear prosthesis, a totally new design approach is utilized. Such design approach is, unfortunately, not backward compatible with existing cochlear implant devices and cochlear electrode arrays. However, as will be evident from the description that follows, the benefits provided by the miniature, low power prosthesis of the present invention far outweigh the disadvantages for those patients who need such a prosthesis.

The features and advantages of the cochlear prosthesis described herein may be summarized as follows:

(1) Fully Simultaneous Stimulation and analog processing is not supported (four simultaneous channels maximum), thereby greatly simplifying the electronic circuitry needed within the prosthesis.

(2) Back compatibility with previous devices is not supported, again simplifying the circuitry needed.

(3) Support for Radial stimulation is provided, thereby offering increased selectivity.

(4) Low Compliance Electrodes are provided that reduce power.

(5) The "Lock" requirement is removed which allows the system to operate asynchronously, which also greatly simplifies the circuitry.

(6) A connector on the electrode with active electronics in each contact is provided. This simplifies the electronic circuitry that must interface with the electrode contacts, and allows the electrode array to be detached from the electronic housing, if needed (e.g., to replace a defective or depleted battery).

(7) The need to use a capacitor to provide capacitive coupling for each contact is eliminated. The function provided by the coupling capacitor is advantageously replaced by a current servo, as explained below.

In short, the above features provided by the invention dramatically reduce power consumption and system size. The design allows implementation with either analog or digital processing. The removal of the back-compatibility requirement greatly reduces the system complexity.

It is also to be noted that while the following description is written in the context of a one dimensional electrode array, it can easily be applied to a multidimensional array(s) of electrodes. Unidimensional and multidimensional electrode arrays, as taught by the present invention, may be applied to a multiplicity of neural stimulation systems such as cochlear, retinal, brain, spinal and organ systems.

Figure 2:
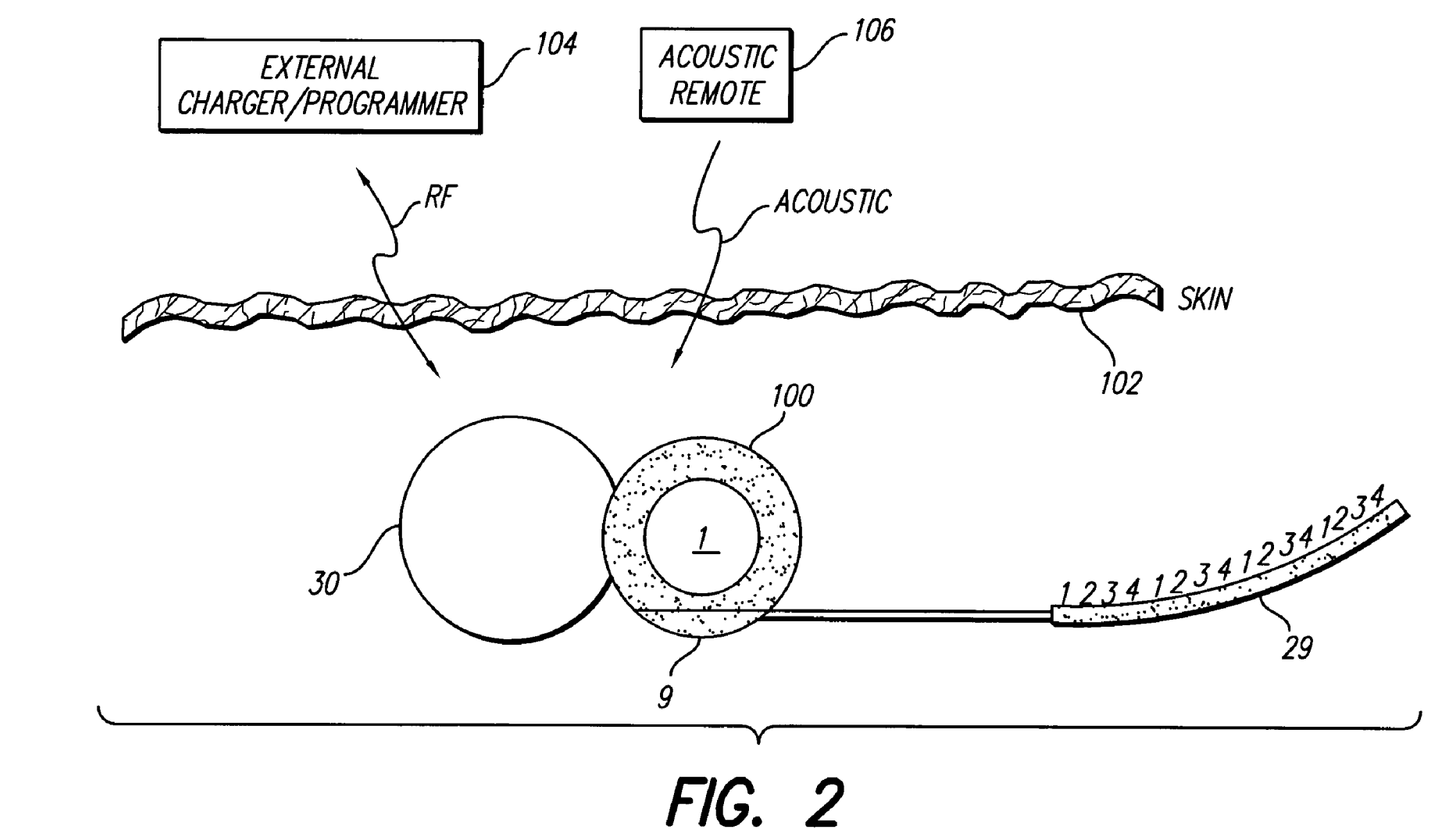
FIG. 2 is a diagram that illustrates the physical arrangement of the main elements of the invention.

Turning first to FIG. 2, the components of the present invention are illustrated. A hermetically sealed housing 100 is adapted to be implanted under the skin 102 of a patient. The housing 100 includes electronic circuitry (not shown in FIG. 2, but functionally depicted in FIG. 1) coupled to an active electrode array 29 through a connector 9. The active electrode array 29 includes a plurality of groups of medial/lateral pairs of electrodes. In a preferred embodiment, the connector 9 has five feed-through connectors 15 through which five different signal conductors included within the active electrode array 29 are connected to the circuitry within the housing 100. More feed-through connectors 15 may be used, as required. The five signal conductors included within the active electrode array 29 are connected to four groups of four medial/lateral pairs of electrodes, as explained below. A subcutaneous microphone 1 is attached to the main body of the housing 100. (Other types of subcutaneous microphones or in-the-ear-canal microphones may be used in lieu of, or in addition to, the microphone 1 attached to the housing 100.) An RF coil 30 is also attached to the housing, and is electrically connected to the circuitry within the housing.

An external (non-implanted) charging/programming unit 104 sends and receives RF signals to and from the RF coil 30, and hence to and from the implanted circuitry within the housing 100. Such signals are used to charge a battery within the housing 100 and/or to program the circuitry within the housing, as is known in the art. Acoustic control signals may also be sent to the implantable microphone 1 from an external acoustic remote control 106. Such acoustic control signals are typically used by the patient to alter the operation of the cochlear prosthesis within prescribed limits, e.g., to adjust the volume or sensitivity.

Next, turning to FIG. 1, the operation of the prosthesis provided by the present invention will be explained. Acoustic energy between 100 and 6000 Hz enters transcutaneously through a subcutaneous microphone 1 in the main body of the implant (and/or through other types of microphones, not shown). This acoustic energy consists of sound to be processed and sent to the patient, as well as narrow band phase-shift-keyed commands (6 KHz) for device control and programming. The microphone signal is amplified by amplifier 2 approximately 20 dB and sent to either analog or digital front end circuitry for preprocessing. A Remote PSK demodulator 3 always searches for PSK data. Demodulated command data is sent to a digital Microprocessor Control Unit (MCU) 4 for decoding. The presence of the command data will wake up the MCU 4 if it is asleep. The MCU 4 can be commanded into various modes of operation by these commands. Such modes include at least: (1) a serial boot mode; (2) a battery maintenance mode; (3) a fitting mode; (4) a sleep mode; and (5) a normal operating mode with a remote control.

Still with reference to FIG. 1, after pre-amplification or digitization, the first step in the processing chain is a bulk automatic gain control circuit 5. This automatic gain control brings the signal into the dynamic range of an Acoustic Processing Bank 6. The Acoustic Processing Bank 6 includes 1-64 configurable filters and envelope detectors, or equivalent taps for envelope information. Typically, a contact is provided for each tap. If there are more electrodes than taps, then variable sized contacts or optimal selections of electrodes can be exploited. Having more taps than contacts (a concept known as "virtual electrodes") is not supported in this architecture because it would require more and scalable current sources. Note that virtual electrodes require a mechanism to send single acoustic tap information to a multiplicity of electrode array contacts that are "scaled" to the position in the array or the weighting of the contact. (In a representative cochlear stimulation system, for example, disclosed in U.S. Pat. No. 6,002,966, incorporated herein by reference, this is done by storing weights for each temporal-spatial stimulus nexus.) Additionally, even though virtual electrodes have shown to be viable for increasing the spatial/pitch resolution for simple signals, their viability for complex acoustic signals due to interaction effects has not been well established. The present invention, on the other hand, supports very sophisticated Acoustic Processing Banks, such as the Silicon Cochlea with Distributed Adaptive Gain, see Sarpeshkar, et al., "A Low-Power Wide-Dynamic-Range Analog VLSI Cochlea". *Analog Integrated Circuits and Signal Processing,* 16, 245-274 (1998), incorporated herein by reference.

A four output cross-point switch 7 allows the selection of any four of the available taps to be routed to any output. A full cross-point switch is preferred for the purposes of adjusting to patient pathology, correcting electrode position, and allowing drivers to be interspersed along the array to reconfigure for partial device failures and produce arbitrary longitudinal bipolar drive configurations. Four outputs are selected because of the ability to implement a practical electrode connector with five contacts. Such a contact may be substantially as described in U.S. patent application Ser. No. 09/455,046, filed Dec. 6, 1999, now issued as U.S. Pat. No. 6,321,126, incorporated herein by reference. Additionally, with only five contacts, the number of wires is reduced over what has previously been required, and this also allows the wire gauge to be increased, all of which has reliability and surgical implications. Additionally, while some might be concerned that having only four simultaneous stimulation sites is a limitation, it is believed that four simultaneous stimulation sites may in reality be close to the maximum number of channels that can be used while still avoiding excessive interaction. Nonetheless, as the connector and electrode technology evolves, the number of simultaneous electrodes may be increased, if such proves to be beneficial. The major disadvantage of providing only four simultaneous drives is the resulting limitation on only being able to drive two true longitudinal bipolar channels simultaneously. Such may or may not be an issue depending upon whether radial stimulation modes are more efficacious for a majority of patients.

After the cross-point switch 7, a Log circuit 8 takes the logarithm of the signal. The Log function approximates a patient's perception of acoustic loudness as a function of current. While the Log function does not represent a perfect predictor of the patient's or subject's perception of acoustic loudness, it is one of the best predictors that has been found that is clinically efficacious. This is due, in large part, to the patients' ability to hear through loudness variations and various forms of compression.

The output of the Log circuits 8 are summed in summing circuit 12. The output of summing circuit 12 is compared with relevant digital data obtained from the MCU 4, which relevant digital data is first converted back to analog data with a digital-to-analog converter (DAC) circuit prior to the comparison.

Next, still with reference to FIG. 1, the log of the acoustic signal is mapped into the patient's electrical dynamic range by a Mapper circuit 9A. The Mapper circuit 9A modifies the signal by two constants (A*input+K) that are independently derived for each channel based upon the behavioral threshold and most comfortable level of each stimulation site. The constants A and K are also dependent upon the patient's or subject's volume control and input dynamic range control, and can be modified up to 10 times per second.

The output of each Mapper circuit drives a Current Source 10. The Current Source 10 is coupled through an optional electrical failure protection capacitor 14 to the Active Contacts 16 in the Electrode Array 29. The Current Sources 10 are usually open (and thus represent an infinite impedance) and are controlled by Pulse Generators 13, and ultimately by the MCU 4. The Current Sources 10 operate in one of the following modes: (1) positive (+) current; (2) negative (−) current; (3) open; (4) short to ground; and (5) 500 kilo-ohm leak to ground. Current source noise is controlled such that 64 monotonic resolvable steps are available to the patient with a current range of 3-30 dB (referenced to 1 μA) over a maximum current range of 20 to 2000 μA. The slew rate of the output currents from the Current Sources 10 is between about 1-10 V/μS with an assumed circuit of a series 1.0 pH inductor and a load of 10 to 100 nanofarads with an impedance in the range of 500-20,000 ohms. The current sources 10 obtain their operating power from either a battery or a fast tracking Buck and/or Boost converter 11, depending on the maximum compliance voltage required by electrode technology and stimulation strategy. A fast tracking converter, if used, should have the ability to track the speech envelope to maximize efficiency. Using multiple Buck/Boost converters does not offer a significant advantage because the varying compliance voltage requirements throughout the cochlea are minimized through the use of variable pulse-width capability and variable contact size. Representative maximum compliance voltages required as a function of electrode configuration are:

1. 16 Channel and Platinum Contacts (16 Volts).
2. 16 Channel and Coatings (3 Volts).
3. 64 Channel, Coatings and Small Contacts (9 Volts).

The Pulse Generators 13 which control the Current Sources 10 receive commands from a Pulse Table in the MCU (4). The use of pulse tables is explained in the referenced patents and patent applications. A given Pulse Generator 13 is commanded from the MCU to select a specific acoustic tap (filter) and to turn on a set of Active Contacts 16, each of which can enable their respective Medial and/or Lateral Contacts. The Pulse Generator 13 coordinates the detailed timing and current drive required to keep charge in balance on individual contacts and disallows contact switching until the charge is balanced. The Pulse Generators communicate to the Active Contacts 16 over the same line that the Current Sources 10 use. This is done by sending digital data at a frequency much higher than the stimulus current transitions with no DC offset as guaranteed by another small capacitor 14.

Figure 3:
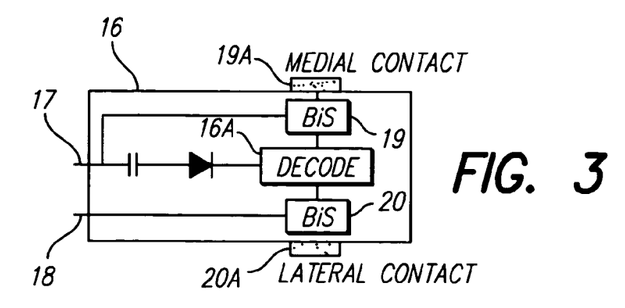
FIG. 3 illustrates the medial and lateral contacts and electrical circuitry carried on and within the active electrode array that is used with the invention.

As seen in FIG. 3, the Active Contacts 16 of the active electrode array 29 have a Current Input line 17 from a specific Current Source 10 and Pulse Generator 13, and a Reference Input line 18 from an Indifferent Current Driver 21. The Current Input line 17 carries a data stream that is decoded in a Decode circuit 16A by each Active Electrode 16 in order to control Bilateral Switches (BiSW) 19, 20 so as to connect or disconnect a Medial Contact Plate 19A to the Current Source line 17 and/or to connect a Lateral Contact Plate 20A to the Indifferent Current Source 21 through the Reference Input line 18. The Reference Input line 18 is used to provide a ground for the decode circuitry 16A and also can be connected to the Lateral Contact Plate 20A as mentioned above. When both the Medial and Lateral Contact Plate are connected, Radial Stimulation is activated, providing potentially a more selective stimulation source. Rectification of a very small amount of power occurs to provide operating power for the Decode circuit 16A and to bias the Bilateral Switches 19 and 20. The current is kept very small so that if there is a failure of the contact, only a small amount of direct current leakage will leave the contact. Hence, when the leakage current is sufficiently small, this type of failure does not require explant.

Figure 4:
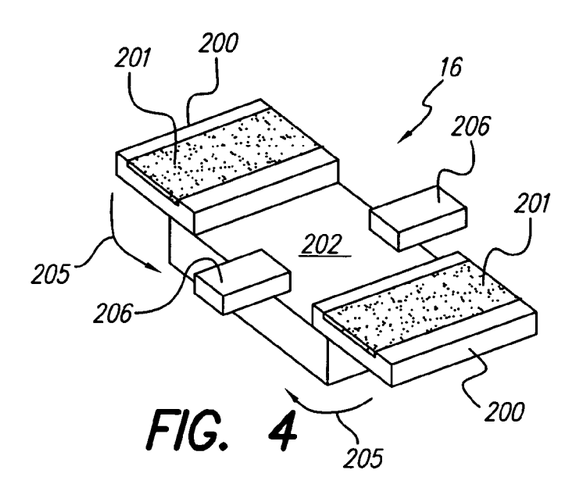
FIG. 4 depicts the manner in which the electrode contacts are fabricated using active cells.
Figure 5:
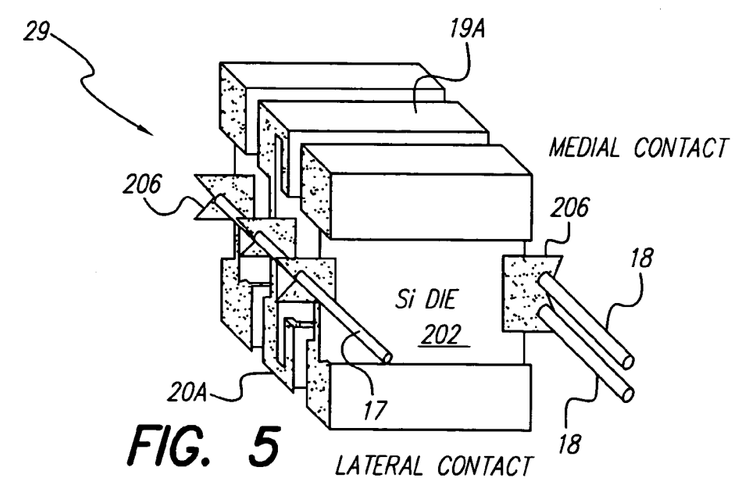
FIG. 5 illustrates the manner in which the active cells are stacked together in order to form the active electrode array.

Turning next to FIGS. 4 and 5, the fabrication of the active electrode array 29 is illustrated. The Active Electrodes 16 provided within the array 29 comprise hermetically sealed active circuits fabricated on a single silicon-on-sapphire (aluminum oxide, AIO) die, with four platinum electrical connections that leave or exit the hermetic space—two connections for contact plates 19A and 20A and two connections for inputs through signal lines 17 and 18 (see FIG. 3). The hermetic seal is preferably achieved with an aluminum oxide coating that is placed directly over the silicon portion of the die, whereas the sapphire substrate is inert (so it does not need to be coated). A void-free silastic over-coating may also be used to protect the aluminum oxide from etching due to possible acidic build-ups resulting from stimulation. Alternatively, a ceramic housing may be provided having contacts that are laser welded onto the ceramic to seal the device.

FIG. 4 illustrates the fabrication of one active electrode 16 of the active electrode array 29. Platinum (Pt) contacts 200 are welded to a silicon die 202 on which appropriate circuitry has been fabricated to perform the function of the bilateral switches 19 and 20 and the decode circuit 16A. The contacts 200 are coated with aluminum oxide (AIO). The oxide is etched off of the contacts 200, leaving an exposed surface area 201. The exposed contacts are then bent over the edge of the silicone die 202, in the direction of the arrow 205, thereby forming the medial and lateral contacts 19A and 20A. Platinum lobes 206, 207 are also attached to the silicone die 202 to allow electrical contact with the circuitry formed thereon.

FIG. 5 shows the stacking of several of the active electrodes formed in FIG. 4 into a bank of electrodes. The wires 17 and 18 are attached, e.g., through a crimping process, to the Platinum lobes 206. The wires themselves serve as a flexible spine support for keeping the individual sections (FIG. 4) separated from each other. Alternatively, flexible spacers may also be inserted in between the individual electrode sections.

Once the Active Electrodes 16 are stacked together, they are also molded with silastic into the electrode array 29. Two indifferent wires 18 and one wire 17 from the driver are connected to each Active Electrode. The connection is made through a splice and crimp to the lobes 206 protruding from the silicone die. Two indifferent wires 18 are used for reliability in the event that one fails. A 64-channel electrode array is arranged such that different banks overlap every millimeter. This arrangement advantageously lends itself to several configurations:

1. Up to 16 electronically variable size contacts (0.25, 0.50, 0.75, or 1 mm) or 32 variable size contacts (0.25 or 0.50) may be employed.
2. Up to 2 longitudinal bipolar contacts, with spacing of 1-16 mm in 1-mm increments, at up to 32 sites may be utilized.
3. Up to 4 radial semi-bipolar (same ground for all contacts) at up to 64 sites may be offered.
4. Up to 4 simultaneous monopolar electrodes at up to 64 sites may be offered.
5. Up to 4 simultaneous radial electrodes with common ground or rib electrodes may be provided.
6. Up to 1 non-simultaneous true bipolar stimulation site may be offered.

Should any one bank of active electrodes fail, one 1-mm section of the electrode array will be out of commission. Moreover, it is noted that each, or at least one, active electrode in each bank may have a built in capacitive strain gauge incorporated therein. This gauge measures the stress across the die indicating the stress setup by the attachment wires and cochlear structures contacting the array or contacts. Such sensors (strain gauges) further help surgeons perform a low stress insertion of the array, and also detect any significant problems during insertion. The output signal(s) of the sensors are typically scanned by having the current sources issue a sinusoid current and then measuring the phase shift with the Back Telemetry Measurement System.

Returning to FIG. 1, it is seen that the Indifferent Current Source 21 (also referred to as an Indifferent Current Driver) drives either an Indifferent Case Electrode 23, or the Lateral Contacts 20A of the Active Electrodes when commanded. A Bilateral Switch 22 under MCU control enables the Indifferent Case Electrode 23. The Pulse Table in the MCU 4 controls both the Indifferent Current Source 21 and the Bilateral Switch 22. The capability of the Indifferent Current Source is the same as the other Current Sources 10, except than it can sink or source up to 8 mA.

A Back Telemetry Measurement System 39 measures voltages on any one or two sets of contacts differentially. The gain of a differential amplifier 40 can be set to 1, 3, 10, 30, 100, 300 or 1000. The recovery time of the amplifier 40 is less than 35

μS. A 9-bit ADC 41 samples at up to 60K samples per second and stores the results in memory circuits included within the MCU 4.

An RF coil 30 receives power and may transmit back telemetry data. The received power is rectified by diode D1 and powers a linear Lithium Ion Battery Charger 33 to charge an implanted battery 34. A Battery Protection Circuit 35 protects the battery from conditions such as over charge and over-discharge, automatically disconnecting the source or load when necessary. The system can still operate from an external source through the coil 30 if the battery is disconnected. A Buck Converter Circuit(s) 36 derives the necessary power supply voltages from the battery voltage that are required for operation of the prosthesis.

A Back Telemetry Transmitter function is included within the MCU 4. An RF carrier with digitally encoded modulated data is generated by the MCU 4. Such modulated RF carrier is transmitted through coupling capacitor 31 onto back telemetry signal path 32 to antenna coil 30, where it is transmitted and ultimately received by an external system. A programming adapter 104 and/or 106 (FIG. 2) has an acoustic transducer for sending data to the prosthesis, and a Back Telemetry Receiver and decoder for receiving data back from the prosthesis. The programming adapter is designed such that it can operate at a distance of up to one meter radiating through the RF coil 30 alone. An alternative mode of operation provides that the Back Telemetry Transmitter simply sends a short duration high amplitude RF carrier pulse that can be received at a distance from the body by a hand-held remote unit. This provides patients or care-givers knowledge of the system status and system modes required of the fully implanted system.

The MCU 4 is self-clocked off an internal crystal 37, thereby advantageously eliminating the need to obtain "lock" which has traditionally been required by existing implantable cochlear stimulator systems. The internal crystal 37 also provides a clock signal from which the RF carrier signal (for back telemetry) may be derived. The system thus runs entirely asynchronous relative to outside support units. For binaural applications, an acoustic command and back telemetry can periodically synchronize two systems, as required, if the systems are equipped with the ability to detect the presence of an external Back telemetry carrier. Advantageously, the MCU 4 does not need non-volatile memory since it always has battery voltage. Accordingly, the MCU is able to perform a serial boot at the clinic with the fitting system over the acoustic data link when the battery is fully discharged.

Psychophysical testing and impedance measurements are performed using pulses generated from a pulse table. In this mode, the input to the current sources must be settable to a fixed value so that pulse modulation can be performed.

Figure 7:
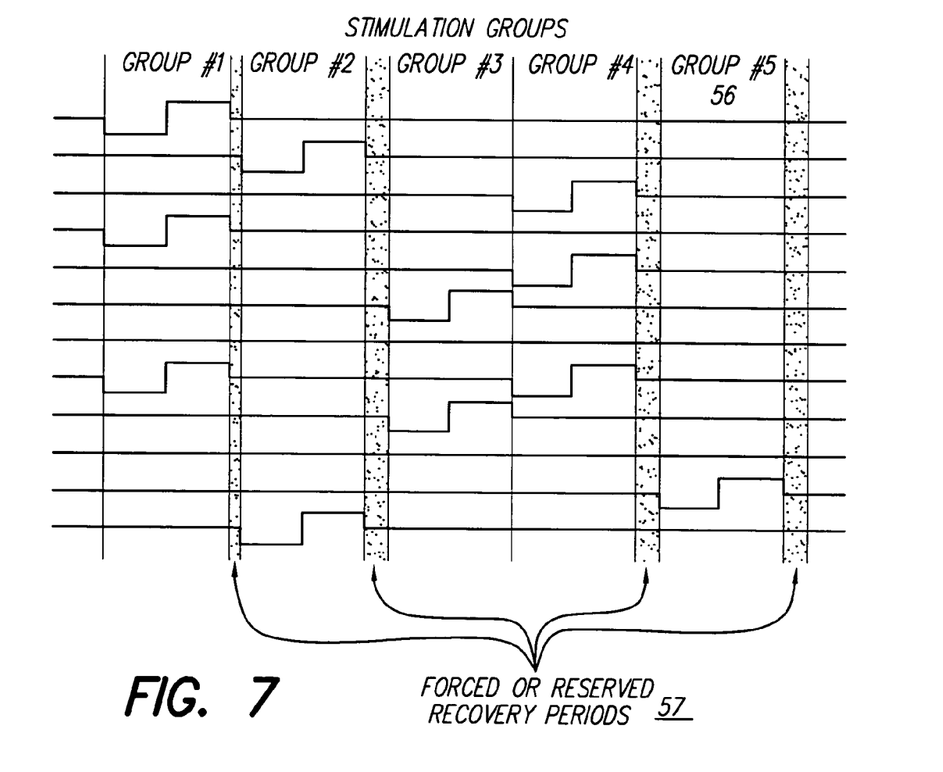
FIG. 7 is a timing waveform diagram that illustrates the stimulation group concept utilized by the invention.
Figure 11:
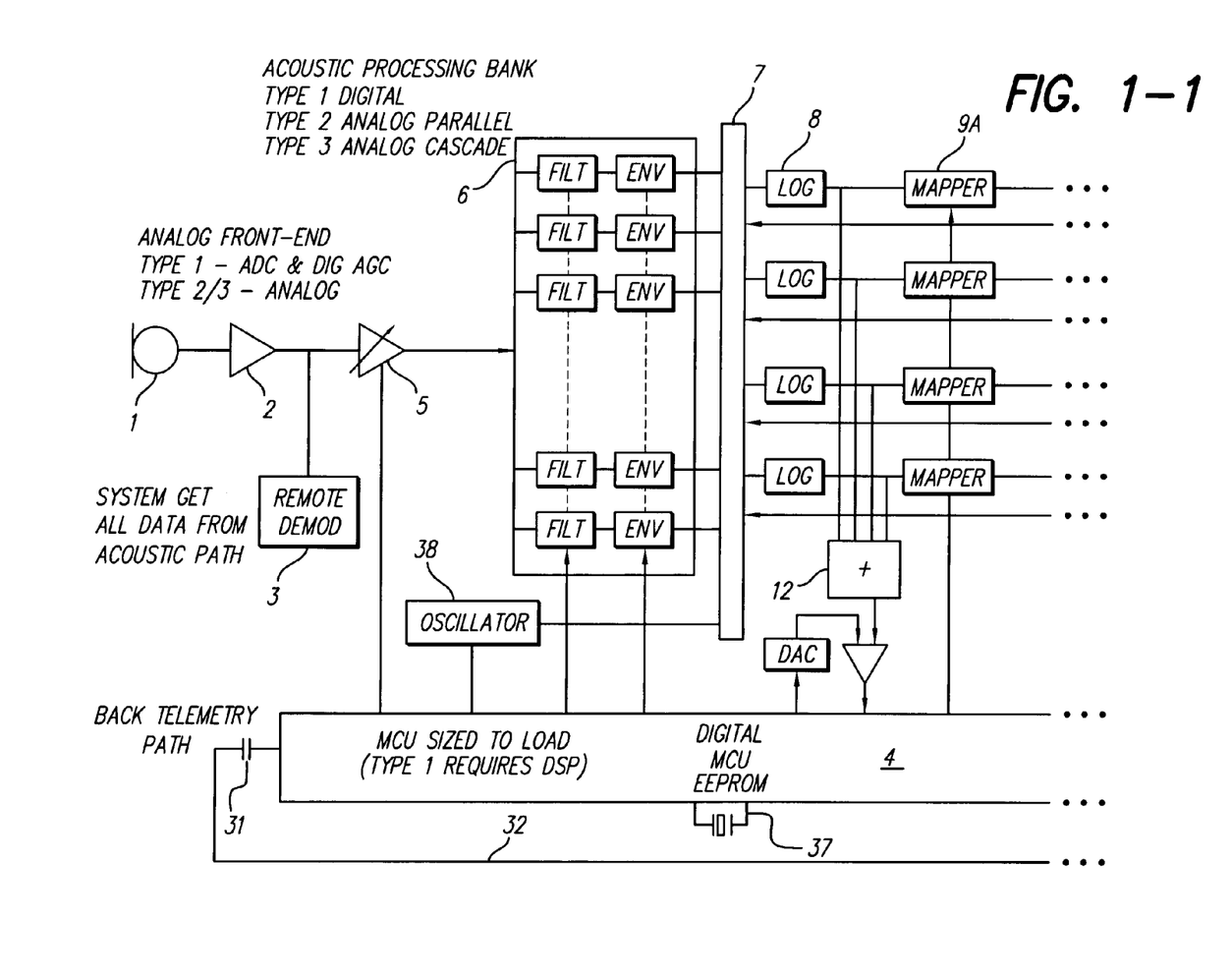
Figure 12:
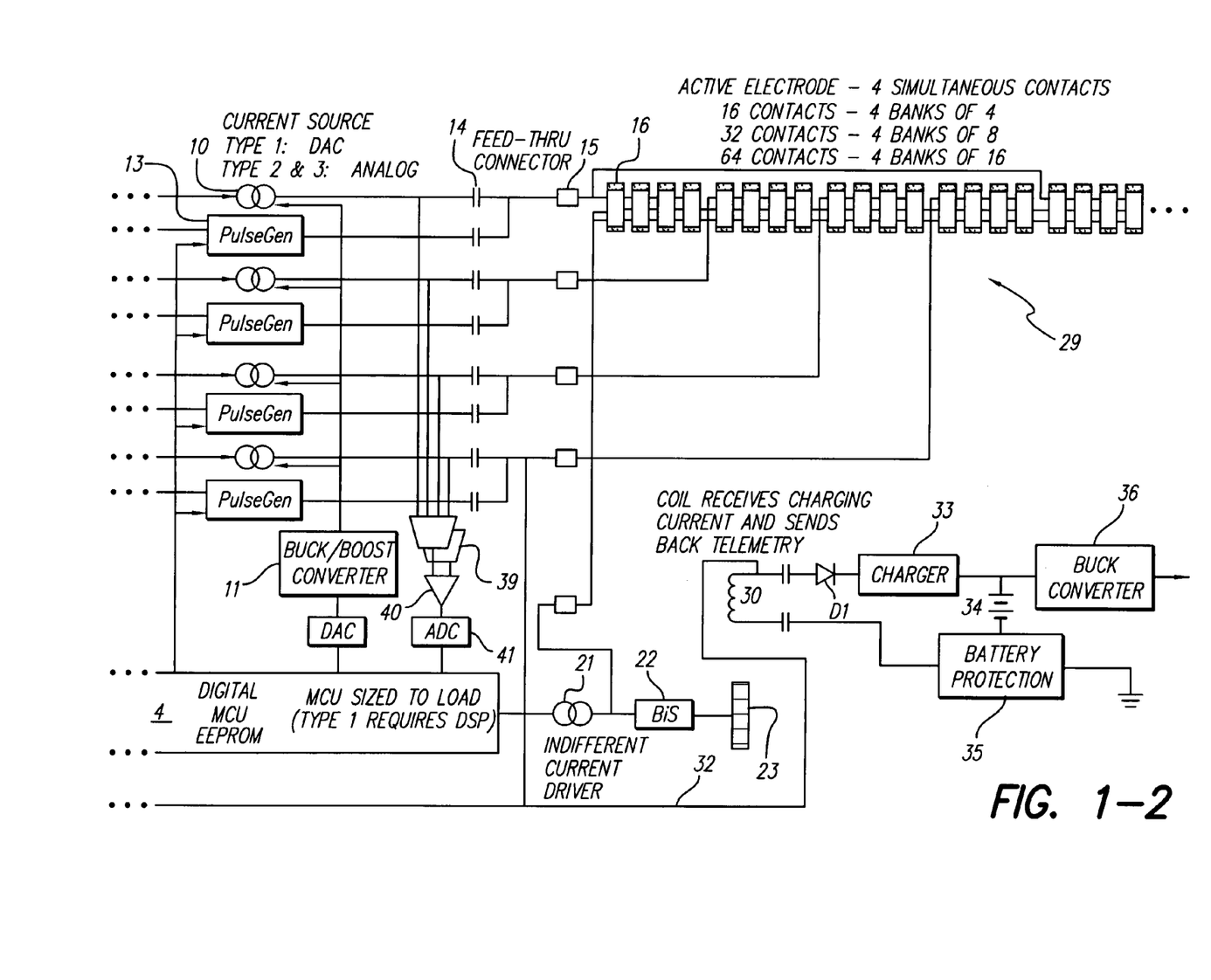

A preferred use of the cochlear prosthesis of the present invention is with simultaneous pulsatile strategies. Simultaneous pulsatile strategies require careful coordination of the outputs in order to avoid interaction and maximize information transfer. In order to understand better how this basic approach operates, the concept of Stimulation Groups will next be described. Simply stated, Stimulation Groups are groupings of contacts that are stimulated together, as illustrated in FIG. 7. The grouping of contacts is determined by electrode interaction and compound action potential measures. Through these measures, the number of actual channels (or useful electrodes) can be estimated by reducing, e.g., a 64×64 interaction matrix. The inverse of this matrix yields a direct measure of interaction guiding the sorting of contacts into stimulation groups. (Typically, when using this approach, a $64^{th}$ order matrix is sparsely filled with measurements, missing data is interpolated, the inverse is taken, and then heuristics are applied to determine the real dimension, or number of channels and stimulation groups, and the degree of simultaneity possible.)

Stimulation groups are then coded into a pulse table, similar to that described in U.S. Pat. No. 6,002,966, or U.S. patent application Ser. No. 09/322,712, filed May 28, 1999, now issued as U.S. Pat. No. 6,289,247, previously referenced. Contacts within stimulation groups are then fit to the patient's dynamic range using objective and behavioral means for a given or optimum pulse-width. From these measures, a target compliance voltage is derived based upon what is expected to be the optimum stimulation rate. (The narrower the pulse widths, the higher the rate, and the higher the compliance voltage.) In order to minimize power dissipation, it is preferred that all contacts be set as close a possible to the target compliance voltage for their respective maximum stimulation levels. This is typically accomplished by varying pulse width. Noting that high stimulation rates and many channels may be necessary, use of the stimulation groups may be necessary. To simplify the system and the interactions, pulse widths of all the contacts within a stimulation group are kept the same. This complicates the software somewhat because it is the software that changes the pulse width and amplitude to reach the target compliance voltage, while the clinician programming the device is able to only increase (or decrease) the amplitude.

The software development and fitting speed are simplified by making modifications to the pulse table that has been used in the past, e.g., as disclosed in the '712 patent application. Further details of the state machine are found in the '712 patent application with the following simplifications and changes.

1. The Data path is simplified because the pulse table has direct access to the filter banks in an unconstrained fashion, the current source has a limited number of configurations; there are no multipliers or shifters with the exception of a possible DAC current range in the digital implementation.
2. The primary complicating factor for software in the system shown in the '712 patent is a uniform pulse width. This is eliminated by the addition of a pulse width entry type associated with each hold bit. This entry significantly reduces memory in strategies with non-uniform pulse widths.
3. An increased memory (2× or 4×) size allows the pulse table generation software to not require extensive optimization.
4. The use of two word commands is permitted across frame boundaries.

The Pulse Table (included within the MCU 4) drives the Pulse Generator. The Pulse Generator is responsible for selecting the correct Acoustic Processing Bank taps, configuring the Current Source and then sending a code to the Active Electrodes.

Codes to the Active Electrodes are of special concern because they require that each contact within a bank have a unique identification (ID) code. For a 16-contact system, this requires 4 ID's; for a 64-contact system, this requires 16 ID's. Code is implemented in any of three ways: electrically fusible links, laser fusible links, or hard-wire connection performed during IC Mask operation. Charge deposition links are not used because of possible moisture issues.

The code consists of an identification pre-amble which includes 2-bit positions for each contact in the bank (e.g., 0001 0000 0010 0000 0001 0000 0000 0000 indicating the $6^{th}$ Medial, $13^{th}$ Medial and $13^{th}$ Lateral contact are connected)

and a post-amble with a double parity and a unique end code (AB$_{16}$). The clock is embedded in the codes using Bi-phase or Manchester encoding so that a local oscillator is not needed. If the contact does not receive a valid code, or if its bit position is not set, it is turned off and reset. Within a bank, many contacts may be turned on simultaneously using the same driving signal, thereby effectively forming larger contacts or adjustable area contacts to adapt to the particular patterns of damage or pathology in the patient's cochlea or other tissue. Using the indifferent electrode with connections to various Lateral Contacts can also create patterns of activation.

One feature provided by the present invention is simultaneous N-of-M strategy. The idea underlying non-simultaneous N-of-M strategy is that if an implant device has M physical stimulation sites, only N relevant sites need to be stimulated during each repetition of the stimulus pattern. This has the effect of enabling higher repetition rates and potentially transferring more relevant information to the patient. Enhancing N-of-M with simultaneous stimulation has the potential to transfer even more information to the patient.

In order to make simultaneous N-of-M strategies viable in a practical system, the following issues should be considered:
1. Contacts or stimulation sites must be grouped into statically assigned or dynamically changing stimulation groups. The present invention preferably uses statically assigned groups to reduce the system complexity and power.
2. Any suitable criteria may be used for deciding when a stimulation group should be skipped or temporally re-sequenced. One time-dependent technique that may be used for this purpose is to look at the sound energy (made by using a weighted sum of the logarithms of the sound envelope energy for each stimulation group) in all of the stimulation groups simultaneously, sort the weighted sums for each group and send the top N contributors. This technique of sorting is very expensive in terms of memory and circuitry and power. A second technique is for the system to have an adaptive threshold where N stimulation groups are attempted but will vary from strategy frame to strategy frame. This method is implemented by means of a control loop varying a threshold that uses the energy estimate of each stimulation group as they come up for possible stimulation. Finally, a scheme that incorporates the pyscho-physical masking parameters as a criteria can also be used where the measured transfer function of the neural interface is used to judge the relevance of the stimulation group to the patient. This last method requires models of the neural interface temporal integrators for at least each Stimulation Group.
3. Once Stimulation Groups are determined, pulse widths within the group should be kept identical so as not to change the interactions. Therefore, an additional constraint allows pulse width changes between groups, but not within groups. Intergroup pulse width changes are designed to minimize strategy frame periods while maintaining a constant maximum compliance voltage to minimize power dissipation.

The current sources 10 and 21 used by the present invention are specialized to always charge balance each current pulse delivered on a single contact or a set of contacts. Contact configurations cannot be changed until charge balance is achieved. Charge balance is achieved by first calibrating and then compensating for the bipolar offset of the current source. Calibration of the system is performed by issuing a step function command on the electrode and using the back telemetry system to monitor its decay to thereby determine its transfer function. Once the transfer function is known, the current source is driven to servo the current to achieve a net zero charge balance before allowing the system to proceed, thereby creating a hardware interlock feature. Such hardware interlock feature presents the system from proceeding until charge balance is achieved. Since, in the preferred embodiment, up to four current sources can be operating simultaneously, all four current sinks must be balanced before proceeding.

As mentioned earlier, stimuli preferably occur in Stimulation Groups 56, as shown in FIG. 7 (which illustrates five stimulation groups). Within a Stimulation Group 56, up to four independent current sources, shown, e.g., in FIG. 1, can stimulate selected non-overlapping contacts. After stimulation, there is a forced or reserved recovery period 57 which must elapse before stimulation of the next group. (Note, that for the example shown in FIG. 7, the forced or reserved recovery period 57 between group #3 and group #4 is zero, which the other forced or reserved recovery periods have a finite width.) Each group is controlled by a Pulse Generator 13 that first resets an Integrator in the group and disconnects any medial contacts 19A and optionally lateral contacts 20A. Then, the pulse generator 13 selects the appropriate tap through the cross-point switch 7 (FIG. 1) and connects the selected medial and lateral contacts. The amplitude is determined by the tap where the value is held.

Figure 6:
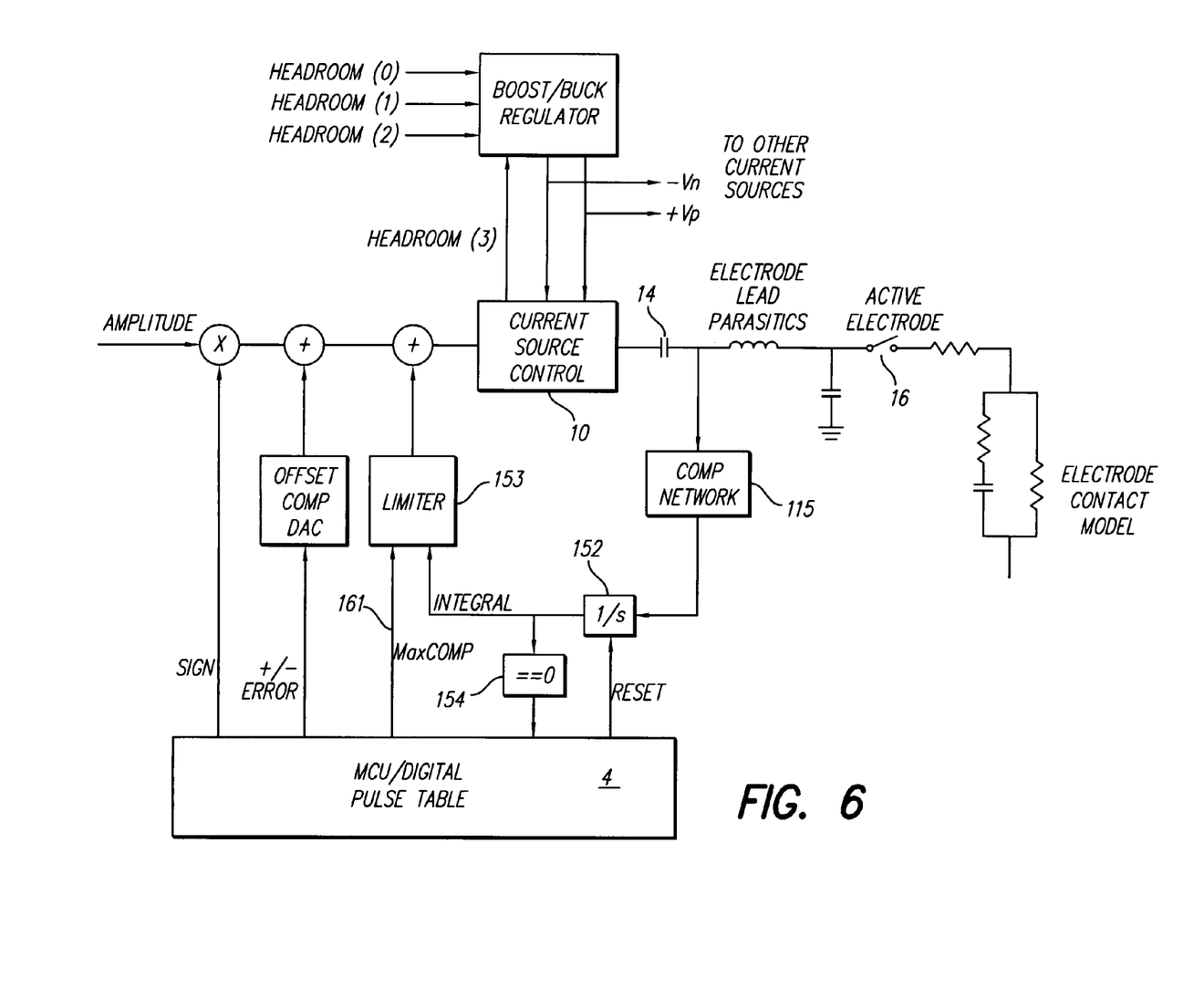
FIG. 6 is a block diagram that illustrates a hardware-based current balancing approach that may be used by the invention.
Figure 6A:
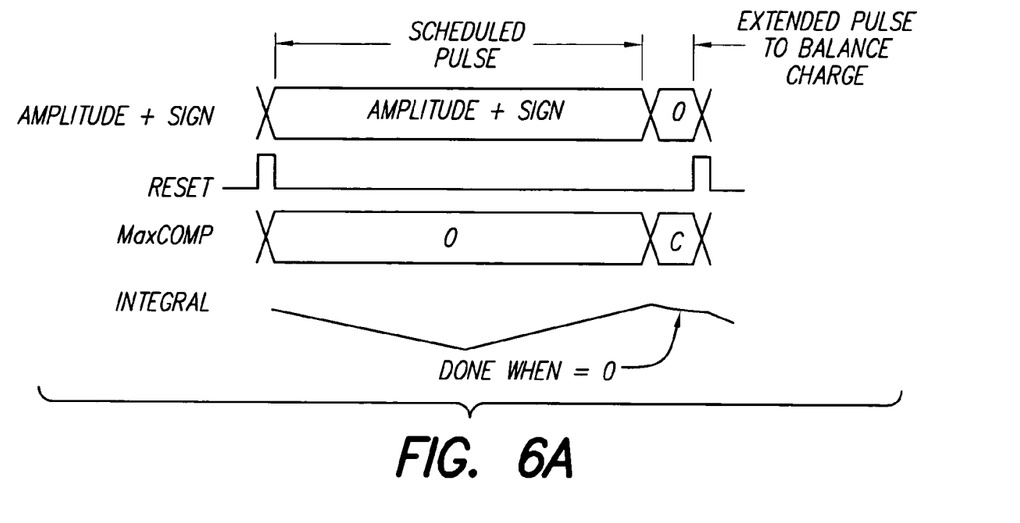
FIG. 6A is a waveform diagram associated with the current-balancing approach illustrated in FIG. 6.

Current balancing is best realized using a current balancing system as is illustrated in FIG. 6, and with waveforms as depicted in FIG. 6A. It is noted that the particular hardware circuitry shown in FIG. 6 represents a particular configuration of the circuitry shown in FIG. 1. That is, the circuitry shown in FIG. 6 illustrates particular elements and components of the circuitry shown in FIG. 1, configured to provide the current balancing function. As seen in FIG. 6, the current balancing system consists of a long-term adjustment found during system calibration and a control loop. The control loop comprises a compensation network 115 that is adapted to the transfer function, a highly accurate integrator 152 to estimate charge, a zero detector 154 to signal charge balance, and a limiter 153 to limit the amount of current that can be driven onto the electrode to balance charge. A Pulse Table included within the MCU 4 normally keeps the limiter 153 set to zero with a MaxComp line 161 set to zero until the Pulse Table expects balanced charge. When balanced charge is expected, the MaxComp line 161 is raised to the maximum level of stimulation needed to achieve balancing.

Analog circuitry used within the prosthesis is programmed via the MCU using DACs that set various parameters. Digital Banks are implemented either by semi-custom logic or by signal processing performed within the MCU/DSP 4 itself. Digital Banks require the addition of a 14-bit effective ADC (in place of 2). In the event the Acoustic Processing Bank is digital, the current source becomes a current mode digital-to-analog converter (DAC). For the analog bank, the current source is an amplifier.

As described above, it is seen that additional complexity has been included in the prosthesis system in order to allow more than sixteen channels and in order to have a connector disconnect. A simplified version of the system can be made by moving the active electrode electronics into the hermetic space of the sealed housing 100 (FIG. 1), and then providing a hermetic feed-through for each electrode contact. Additional simplification may be realized by adding a capacitor in series with each contact, thereby eliminating the need for current balancing electronics.

While the invention herein disclosed has been described by means of specific embodiments and applications thereof, numerous modifications and variations could be made thereto by those skilled in the art without departing from the scope of the invention set forth in the claims.

What is claimed is:

1. An active electrode array located at or near a distal end of an implantable lead, the active electrode array being adapted for use with an implantable tissue stimulating prosthesis, wherein the active electrode array comprises:
   at least four banks of Active Contacts in the active electrode array, wherein each bank of the at least four banks of Active Contacts includes at least one lateral electrode contact and at least one medial electrode contact;
   decoding circuitry built into each bank of Active Contacts in the active electrode array; and
   switching circuitry built into each bank of Active Contacts within the active electrode array, wherein each Active Contact of each bank of Active Contacts may be individually activated by electrode control signals applied to the switching circuitry of each bank of Active Contacts; and
   wherein the switching circuitry of each bank of Active Contacts within the active electrode array comprises a first switch coupled to the decoding circuitry and the at least one lateral electrode contact, and a second switch coupled to the decoding circuitry and the at least one medial electrode contact; and
   wherein the decoding circuitry responds to the electrode control signals and causes the first and second switches to selectively activate one or both of the medial or lateral electrode contacts.

2. The active electrode array of claim 1 wherein the decoding circuitry and first and second switches of each bank of Active Contacts are formed on a substrate die, and wherein the medial and lateral electrode contacts of each bank of Active Contacts are formed on opposing edges of the substrate die, and wherein at least four of said substrate dies are stacked and over-molded with silastic to form the active electrode array.

3. The active electrode array of claim 2 wherein at least one Active Contact within each bank of at least four Active Contacts includes a built-in strain gauge, wherein the strain gauge is adapted to measure stress across the substrate die.

4. An active electrode array located at or near a distal end of an implantable lead, the active electrode array being adapted for use with an implantable tissue stimulating prosthesis, wherein the active electrode array comprises:
   at least four active electrodes, each active electrode having at least four Active Contacts, wherein the Active Contacts include at least one first type of electrode contact and at least one second type of electrode contact;
   decoding circuitry built into each active electrode;
   switching circuitry built into each active electrode, wherein the at least one first type of electrode contact of the Active Contacts of each active electrode and the at least one second type of electrode contact of the Active Contacts of each active electrode may be individually activated by electrode control signals applied to the switching circuitry; and
   wherein the decoding circuitry responds to the electrode control signals and causes the switching circuitry to selectively activate one or more of the Active Contacts of one or more of the active electrodes; and
   wherein the switching circuitry of each active electrode comprises:
      a first switch coupled to the decoding circuitry and the first type of electrode contact, and
      a second switch coupled to the decoding circuitry and the second type of electrode contact; and
      wherein the decoding circuitry and first and second switches of each active electrode are formed on a substrate die, and wherein the first type and second type of electrode contacts of the active electrode are formed on different surfaces of the substrate die.

5. The active electrode array of claim 4 wherein at least four of said substrate dies are joined together to form the active electrode array.

* * * * *